United States Patent [19]

Meijer

[11] 4,003,038
[45] Jan. 11, 1977

[54] THERMAL DISCRIMINATOR FOR SENSING VARIATIONS IN THE HEAT EXCHANGE PROPERTIES OF A MEDIUM

[75] Inventor: Robert S. Meijer, Montreal, Canada

[73] Assignee: Multi-State Devices Ltd., Dorval, Canada

[22] Filed: June 9, 1975

[21] Appl. No.: 585,445

[52] U.S. Cl. .................. 340/227 D; 307/310; 340/244 R; 340/239 R
[51] Int. Cl.² ................................ G08B 21/00
[58] Field of Search ....... 340/239 R, 244 C, 244 R, 340/228 R, 227 D; 307/118, 310; 317/148.5 B, DIG. 1, DIG. 3

[56] References Cited
UNITED STATES PATENTS

| | | | |
|---|---|---|---|
| 3,343,004 | 9/1967 | Ovshinsky | 307/310 |
| 3,402,131 | 9/1968 | Futaki et al. | 252/512 |
| 3,766,395 | 10/1973 | Keir | 340/244 R |
| 3,781,839 | 12/1973 | Bodge | 340/239 R |
| 3,878,541 | 4/1975 | Dodson | 340/228 R |
| 3,882,728 | 5/1975 | Wittlinger | 307/310 |

*Primary Examiner*—Glen R. Swann, III
*Attorney, Agent, or Firm*—Spencer & Kaye

[57] ABSTRACT

A thermal discriminator including two temperature sensitive switching devices having substantially identical electrical characteristics and exhibiting regenerative switching at a power level which is dependent on the temperature sensed by the switching devices. Both switching devices are exposed to the same ambient temperature in a surrounding medium but only one of them is exposed to variations in the heat exchange properties of the surrounding medium. Sufficient power is applied to both switching devices from an increasing voltage source to cause the switching devices to dissipate about the same amount of heat under certain conditions of the medium so that both switching devices would normally switch substantially simultaneously. A coupling device is connected between the two switching devices and includes regenerative switching in one of the switching devices in response to unbalance in the heat dissipated by the switching devices due to variations in the heat exchange properties of the surrounding medium from such conditions of the medium, and so inhibit the other switching device from switching. Discriminating means are connected to the two temperature sensitive switching devices for sensing which one of the switching devices has switched as an indication that the heat exchange properties of the medium have changed.

8 Claims, 4 Drawing Figures

THERMAL DISCRIMINATOR FOR SENSING VARIATIONS IN THE HEAT EXCHANGE PROPERTIES OF A MEDIUM

BACKGROUND OF THE INVENTION

This invention relates to a thermal discriminator for sensing variations in the heat exchange properties of a medium, and more particularly to a discriminator for sensing variations in the flow of a fluid medium, such as air or liquid or for sensing the presence or absence of a liquid as an indication of the level of a liquid in a reservoir.

Various devices have been used in the prior art for sensing variations in the flow of a fluid medium or for sensing liquid level. For sensing fluid flow, for example, various mechanical impact devices have been used. However, they present substantial interference with the fluid flow. Generally, the mechanical devices, whether used for sensing fluid flow or for fluid level detection, have poor response characteristics and cannot sense relatively small variations in the heat exchange properties of the surrounding medium. They are also susceptible to nuisance operations and subject to wear.

Negative and positive temperature coefficient devices have also been used for sensing variations in the heat exchange properties of a medium. Such devices are normally placed in contact with the medium and the temperature sensed by the devices varies in accordance with the rate at which the medium is drawing heat away from them. Negative and positive temperature coefficient devices can be used for measuring fluid flow or for sensing fluid levels. The above prior art arrangements are, however, very sensitive at ambient temperature and power supply variations and means are required for providing adequate compensation for such variations. Ambient temperature compensation may be effected by providing a bridge circuit including a second temperature sensitive device which is exposed to ambient temperature but not in contact with the surrounding medium as disclosed in Canadian Pat. No. 582,848 issued Sept. 8, 1959. However, bridge circuits generally have a very small output which cannot be sensed directly to control an alarm device and complicated circuitry must be used to amplify their output signal.

SUMMARY OF THE INVENTION

It is therefore the object of the present invention to provide a thermal discriminator for sensing variations in the heat exchange properties of a medium which is relatively immune to ambient temperature and power supply variations.

The apparatus, in accordance with the invention, includes a first and a second temperature sensitive switching devices having substantially identical electrical characteristics and exhibiting regenerative switching at power level which is dependent on the temperature sensed by such switching devices, both switching devices being exposed to the same ambient temperature in a surrounding medium but only one of them being exposed to variations in the heat exchange properties of the surrounding medium. Means are provided for applying to the switching devices sufficient power from an increasing source of voltage to cause the switching devices to dissipate about the same amount of heat under preset conditions of the medium so that the switching devices should switch substantially simultaneously as the voltage applied across them increases from zero. A coupling device is interconnected between the first and second switching devices for inducing regenerative switching action in one of the switching devices in response to unbalance in the heat dissipated by such switching devices due to variations in the heat exchange properties of the surrounding medium from such conditions and so inhibit the other switching device from switching. A discriminating mean is connected to the first and second switching devices for detecting which one of said switching devices has switched as of an indication that the heat exchange properties of the medium surrounding such switching devices have changed.

The coupling device may be any unidirectional or bidirectional conducting element such as a resistor, a capacitor, a diode or a transistor.

The discriminating means may be any means capable of detecting which one of the temperature sensitive switching devices has switched. This operation may be easily done by conventional digital circuits.

A resistor is preferably connected in series with each temperature sensitive switching devices across the voltage source and the maximum value of the source and the value of the resistors are selected to ensure that, under normal operating conditions, the switching devices will switch in accordance with a predetermined sequence.

The thermal discriminator may be used to control a triac connected in series with a medium conditioning device or an alarm device. The gate of the triac is normally controlled by a silicon controlled rectifier, which acts as the discriminating means. However, low power loads, such as alarm devices, may be controlled directly by the silicon controlled rectifier.

BRIEF DESCRIPTION OF THE DRAWINGS

The invention will now be disclosed, by way of example, with reference to preferred embodiments illustrated in the accompanying drawings in which.

DETAILED DESCRIPTION OF THE PREFERRED EMBODIMENTS

Figure 1:
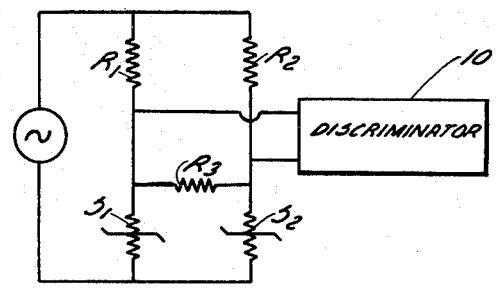
FIG. 1 illustrates a block diagram of a thermal discriminator in accordance with the invention.

Referring to FIG. 1, there is shown a block diagram of a thermal discriminator in accordance with the invention. The discriminator comprises a first temperature sensitive switching device $S_1$ connected in series with a resistor $R_1$ across a source of periodically increasing voltage such as a conventional 110 volts A.C. power line, a second temperature sensitive switching device $S_2$ having substantially the same electrical characteristic as the first switching device $S_1$ and connected in series with a resistor $R_2$, a coupling device in the form of a resistor $R_3$ interconnecting the switching devices $S_1$ and $S_2$, and a discriminating device 10 having one input connected to the connecting point of switching device $S_1$ with resistor $R_1$ and a second input connected to the connecting point of switching device $S_2$ with resistor $R_2$.

A number of switching devices, such as the amorphous glass devices transition metal oxide devices (see, for example, U.S. Pat. No. 3,402,131, issued Sept. 17, 1968 to H. Futaki et al.), and certain classes of negative temperature coefficient devices show a regenerative switching action which is strongly dependent on the temperature of the switching device. In most cases elevated temperatures correspond to a reduction in the voltage threshold necessary to cause switching. The expression "regenerative switching devices" as used herein means devices exhibiting avalanche behaviour due to their very high negative temperature coefficient of resistance. As commonly known, most thermal avalanche behaviour is due to a current crowding effect in which current crowding leads to local heating in the device which in turn leads to further current crowding. On completion of this process, most of the device current flows through a very narrow filament in the device. Because of the relatively low resistance of the conducting material, total device resistance becomes quite low. Such devices therefore behave like switches and go from a high resistance to a low resistance state in a very short period of time. The basic switching mechanism of the temperature dependent regenerative switching devices is usually thermal and occurs in response to both Joule heating and the ambient thermal energy. In most cases, switching action is observed when the sum of all energies yields a given temperature at the switching element. In other words, whatever the source of heat, the switching device always switches at an essentially fixed temperature.

In order to detect a change in the heat exchange properites of a medium, both switching devices must be exposed to the same ambient temperature in the medium being monitored. However, one switching device only is exposed to variations in the heat exchange properties of the medium. In a device such as an air flow sensor, as shown in FIG. 1, both switching devices $S_1$ and $S_2$ may be exposed to the stream of moving air but the switching device $S_1$ must be placed in a heat sink so as to render it non-responsive to variations in air flow.

Figure 2:
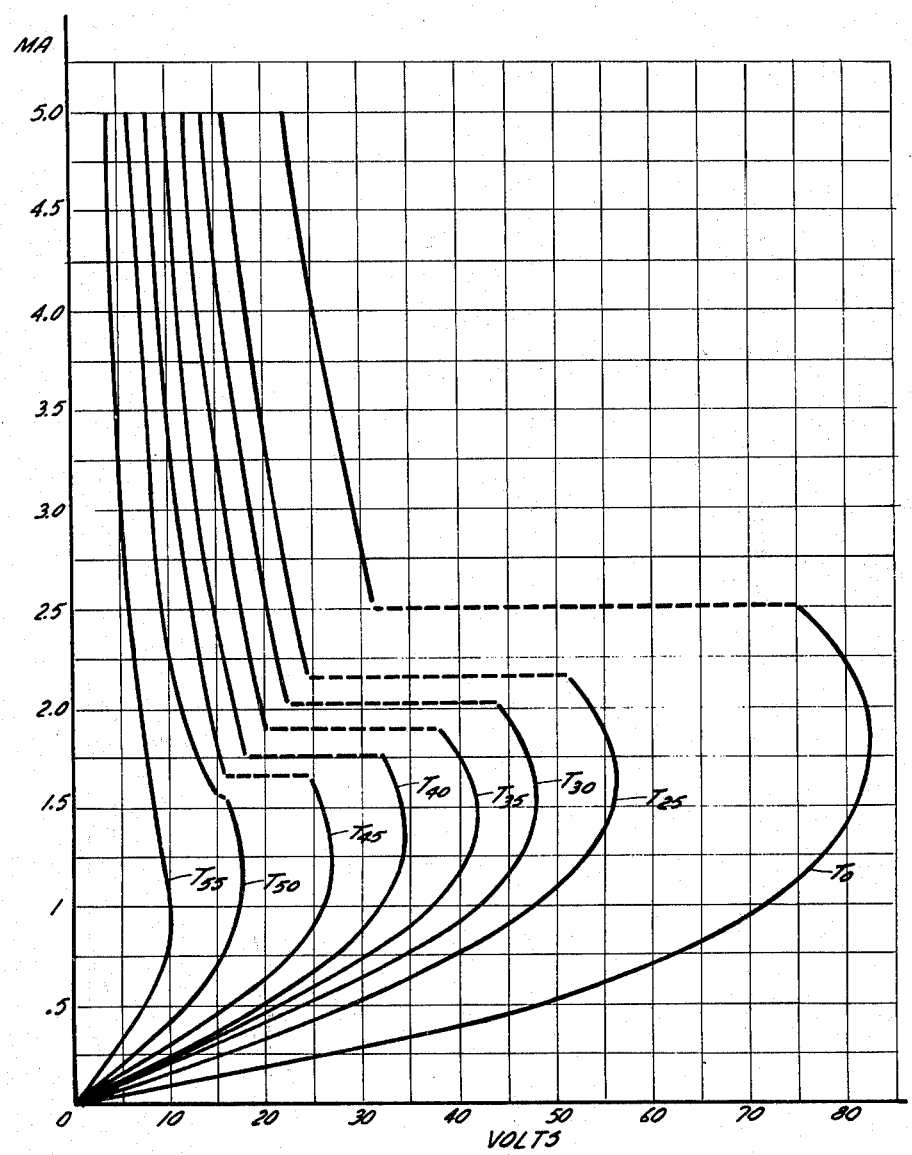
FIG. 2 illustrates the temperature dependent current-voltage characteristics of a vanadium oxide device suitable for use as a temperature sensitive switching device.

Under ideal conditions, with the switching devices $S_1$ and $S_2$ in the medium being monitored and the fan blowing at a preset speed, the amplitude of the A.C. voltage source and the value of resistors $R_1$ and $R_2$ could be selected so that, when the voltage increases from zero, both switching devices would normally switch substantially simultaneously to their low voltage high current value. However, this condition is not easy to obtain in practice because coupling device $R_3$ causes rapid switching of one switching device which in turn inhibits the other switching device from switching as will be disclosed later. The values of resistors $R_1$ and $R_2$ are therefore selected so that one of the switching devices, under normal operating conditions, will switch first and inhibit the other from switching. If such conditions should change the opposite will happen. In an embodiment designed to sense a reduction or loss of air flow, the circuit parameters are set so that switching device $S_1$ switches first and switching device $S_2$ is inhibited from switching. Any reduction or loss of the normal flow of air will cause switching device $S_2$ to warm up whereas switching device $S_1$ will not heat up appreciably because it is in a heat sink. Because switching device $S_2$ now becomes warmer than switching device $S_1$, the voltage required to turn it on is significantly reduced as illustrated in FIG. 2 which shows a series of current-voltage curves $T_0$ to $T_{55}$ representing the characteristics of the switching devices as the temperature varies from 0° to 55° C respectively. If switching device $S_2$ was following curve $T_{25}$, for example, under normal room temperature and a preset air flow, upon a reduction or loss of air flow, switching device $S_2$ will heat up and perhaps follow curve $T_{30}$. The voltage appearing across switching device $S_2$ will thus be reduced and, due to the presence of coupling resistor $R_3$, still more current will flow through switching device $S_2$ and such device will further heat up to eventually drop down to a very low impedance. When this happens, switching device $S_1$ will be short-circuited by switching device $S_2$ and, consequently, switching device $S_1$ will not switch. Thus, a very simple discriminating device 10 may be used for sensing switching of switching device $S_2$ combined with non-switching of switching device $S_1$. Of course, the opposite situation will prevail in an embodiment designed to sense an increase in air flow above a preset value. Switching device $S_2$ will be set to switch first and switching device $S_1$ will be short-circuited under normal operation. However, if the air flow increases, switching device $S_2$ will cool and switching device $S_1$ will switch first.

Figure 3:
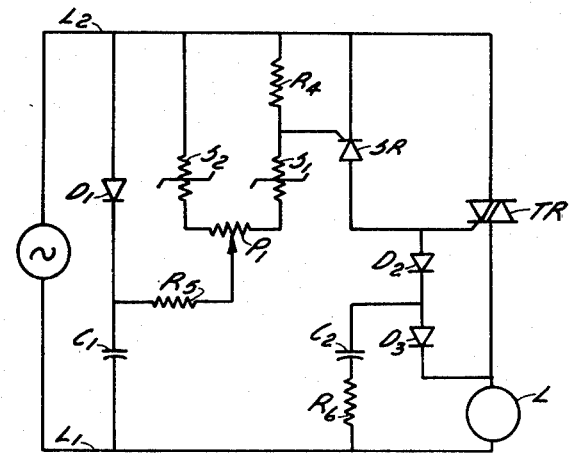
FIG. 3 illustrates an embodiment of a thermal discriminator used for operating a medium conditioning device.

FIG. 3 illustrates an apparatus utilizing a thermal discriminator in accordance with the invention. The discriminator includes switching devices $S_1$ and $S_2$ which are assumed to be both exposed to air flow but the switching device $S_1$ is assumed to be placed in a heat sink so as to render it insensitive to reduction or loss of air flow. A coupling device in the form of potentiometer $P_1$ interconnects switching devices $S_1$ and $S_2$. Such coupling potentiometer is used for the same purpose as resistor $R_3$ in FIG. 1 of the drawings except that it is variable so as to establish the air flow level at which the load L will be de-energized. Under normal air flow, switching device $S_1$ is set to switch ahead of switching device $S_2$ by proper adjustment of the variable tap of potentiometer $P_1$. Whenever the air flow is reduced below the preset level, switching device $S_2$ warms up and switches on before switching device $S_1$ has the opportunity to do so so that switching device $S_1$ remains in its off condition. When this happens, the potential applied to the gate of silicon controlled rectifier SR through the voltage divider including resistor $R_4$, switching device $S_1$, potentiometer $P_1$ and resistor $R_5$ is insufficient to fire the silicon controlled rectifier SR which, in this embodiment, acts as a discriminating means to detect which one of the switching devices $S_1$ and $S_2$ has switched. Triac TR is rendered non-conductive, as it will be explained later, and the load L will be de-energized.

Of course, by interchanging the role of the switching devices $S_1$ and $S_2$, the load may be set to be energized upon reduction of air flow below a predetermined level. In such a configuration, the element indicated as a load may be replaced by an alarm.

Figure 4:
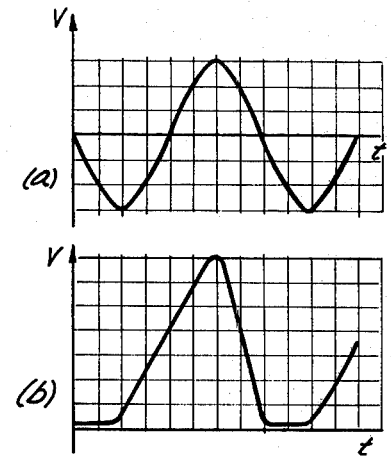
FIGS. 4a and 4b illustrate waveforms associated with FIG. 3.

The firing of silicon controlled rectifier SR and of the triac TR will be more clearly understood with reference to FIGS. 4a and 4b of the drawings. Taking line L2 as a reference which remains at 0 volt, the following will happen as the voltage of the A.C. source shown in FIG. 4a goes to an increasing negative value:

$\phi = 0°$ to $90°$

The voltage on line L1 goes negative to the peak value of the line voltage. This level of voltage is stored in capacitor C1 which is connected in series with diode D1 across the A.C. source.

$\phi = 90°$ to $180°$

The voltage on line L1 returns to zero and the voltage at the junction of diode D1 and capacitor C1, as illustrated in FIG. 4b, goes to about twice the line voltage and is positive with respect to line L1. When the air flow is above the predetermined level, switching device $S_1$ is turned on by that time and there is proper gate current to the silicon controlled rectifier SR from the time switching device $S_1$ fires to about 270°. However, between 90° and 180°, the silicon controlled rectifier SR, even though it has gate current, cannot fire because its anode is negative with respect to its cathode.

$\phi = 180°$ to $360°$

At 180°, the anode of the silicon controlled rectifier SR turns on and, in turn, turns on the triac TR. This arrangement ensures zero firing of the triac TR as is commonly required to reduce interference on the commercial power lines. Normal operation of the triac ensures that it will remain on over the full half cycle that line L1 is positive with respect to line L2, that is 180° to 360°.

$\phi = 360°$ to $540°$

The operation of the triac from 360° to 540° is taken care of by a conventional slaving circuit including diodes $D_2$ and $D_3$, capacitor $C_2$ and resistor $R_6$. As commonly known, capacitor $C_2$ is charged through resistor $R_6$ and diode $D_3$ from 180° to 270° and is subsequently discharged through diode $D_2$ from 270° to 540° to maintain conduction of the triac until the silicon controlled rectifier SR is rendered conductive again at the next cycle of the A.C. source as explained previously.

As it has been seen, the load remains energized as long as switching device $S_1$ turns on. In case of a drop in the air flow level, switching device $S_2$ will fire first and prevent switching device $S_1$ from firing. Since switching device $S_1$ remains in its high impedance state, not enough voltage will be applied to the gate of silicon controlled rectifier SR to render it conductive. Consequently, the load will be de-energized. It will be easily understood that the opposite will happen if switching device $S_1$ is exposed to the air flow while switching device $S_2$ is not by placing it in a heat sink, for example. In such a case, the silicon controlled rectifier will be normally non-conductive and the load L will be de-energized. However, when there is a loss of air flow, switching device $S_1$ will be turned to its low impedance state and the silicon controlled rectifier SR will be turned on and, in turn, will turn on the triac TR to energize the load L. As mentioned previously, the load L may then be an alarm device for indicating the loss of air flow. In the latter case, and in case of low power applications the triac TR may not be required and the load L may be connected in series with the silicon controlled rectifier SR.

The above apparatus has been disclosed only to illustrate an example of a circuitry making use of the thermal discriminator in accordance with the invention. It is to be understood that any discriminating means may be used to sense which one of the switching devices has switched as an indication of a variation in the heat exchange properties of the medium.

It is also to be understood that the coupling device which is shown in FIG. 1 of the drawings as being a resistor may be any bidirectional or unidirectional conducting element capable of inducing regenerative switching in the switching devices in case of unbalance in the heat dissipated by the switching devices due to variations in the heat exchange properties of the surrounding medium. As mentioned previously, such will further unbalance the heat dissipated by the switching devices and rapidly cause regenerative switching of the devices.

Finally, it is also to be understood that the above thermal discriminator is useful not only for sensing a reduction or increase of air flow. It may be useful as a liquid level sensor for sensing the absence or presence of the medium into which switching devices $S_1$ and $S_2$ have previously been placed. In such a case, temperature sensitive switching devices $S_1$ and $S_2$ are normally placed in contact with the liquid medium when the level of the liquid in a reservoir is at a predetermined height. If this level falls, the temperature sensitive switching devices will be out of the liquid and exposed to the ambient air. As the rate of heat removed in air is different from what it is in liquid, this will be sensed by the thermal discriminator. Generally speaking the above thermal discriminator may be used for sensing any variations in the heat exchange properties of a medium.

What is claimed is:

1. A thermal discriminator for sensing variations in the heat exchange properties of a medium comprising:
    a. a first and second switching devices having substantially indentical electrical characteristics and exhibiting regenerative switching at a power level which is dependent on the temperature sensed by said switching devices, both said switching devices being exposed to the same ambient temperature in a surrounding medium but only one of them being exposed to variations in the heat exchange properties of the surrounding medium;
    b. means for applying to both switching devices sufficient power from an increasing voltage source to cause the switching devices to dissipate about the same amount of heat under certain conditions of the medium so that both switching devices would normally switch substantially simultaneously;
    c. a coupling device interconnecting said first and second switching devices for inducing regenerative switching action in one of said switching devices in response to unbalance in the heat dissipated by said switching devices due to variations in the heat exchange properties of the surrounding medium from said conditions, and to inhibit the other switching device from switching; and
    d. discriminating means connected to the first and second switching devices for detecting which one of said switching devices has switched as an indication that the heat exchange properties of the surrounding medium have changed.

2. An apparatus as defined in claim 1, wherein each switching device is connected in series with a resistor and wherein the amplitude of the voltage supplied by said voltage source and the value of each resistor are chosen so that, under preset operating conditions, the devices will switch in accordance with a predetermined schedule.

3. An apparatus as defined in claim 1, wherein said coupling device is a resistor.

4. An apparatus as defined in claim 1, wherein said discriminating means is a digital device.

5. An apparatus as defined in claim 1, wherein said discriminating means is a silicon controlled rectifier which is connected in series with a load across said voltage source and has a gate connected to one of said switching devices.

6. An apparatus as defined in claim 1, used for firing a triac which is connected in series with a load across a voltage source of the alternating current type and has a gate, and wherein said discriminating means is a silicon controlled rectifier connected to said gate of said triac and having a gate connected to one of said switching devices.

7. An apparatus as defined in claim 6, wherein the gate circuit of the silicon controlled rectifier includes capacitor means for storing a predetermined voltage on the gate of the silicon controlled rectifier when its anode is negative with respect to its cathode so as to turn the silicon controlled rectifier on as soon as its anode goes positive with respect to its cathode, thus insuring zero firing of the silicon controlled rectifier and of the triac.

8. An apparatus as defined in claim 7, further comprising a slaving circuit connected to the gate of the triac for maintaining the triac conductive during the negative cycle of the A.C. power source.

* * * * *